United States Patent
Flashner-Barak

(10) Patent No.: US 6,569,459 B2
(45) Date of Patent: May 27, 2003

(54) METHOD OF ADMINISTRATION OF PACLITAXEL-PLASMA PROTEIN FORMULATION

(75) Inventor: Moshe Flashner-Barak, Petach Tikva (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 09/829,744

(22) Filed: Apr. 10, 2001

(65) Prior Publication Data
US 2001/0056070 A1 Dec. 27, 2001

Related U.S. Application Data

(60) Provisional application No. 60/195,912, filed on Apr. 10, 2000.

(51) Int. Cl.$^7$ .............................. A61K 9/14; A61K 9/50; A61F 2/00
(52) U.S. Cl. ........................ 424/489; 424/484; 424/486; 424/499; 424/400; 424/426
(58) Field of Search .................................. 424/489, 484, 424/401, 426, 486, 499; 514/449

(56) References Cited

U.S. PATENT DOCUMENTS

| | | |
|---|---|---|
| 5,407,683 A | 4/1995 | Shively |
| 5,415,869 A | 5/1995 | Straubinger et al. |
| 5,470,311 A | 11/1995 | Setterstrom et al. |
| 5,496,846 A | 3/1996 | Wilson et al. |
| 5,504,102 A | 4/1996 | Agharkar et al. |
| 5,580,575 A | 12/1996 | Unger et al. |
| 5,621,001 A | 4/1997 | Canetta et al. |
| 5,626,862 A | 5/1997 | Brem et al. |
| 5,641,803 A | 6/1997 | Carretta et al. |
| 5,651,986 A | 7/1997 | Brem et al. |
| 5,684,169 A | 11/1997 | Hamada et al. |
| 5,696,153 A | * 12/1997 | Ainsworth et al. ......... 514/449 |
| 5,846,565 A | 12/1998 | Brem et al. |
| 5,888,530 A | 3/1999 | Netti et al. |
| 6,071,952 A | * 6/2000 | Owens et al. ............... 514/449 |

FOREIGN PATENT DOCUMENTS

WO   WO 99/13914   * 3/1999

OTHER PUBLICATIONS

Kuh HJ, Jang SH, Wientjes MG, Weaver JR, Au JL-S. Determinants of paclitaxel penetration and accumulation in human solid tumor. Journal of Pharmacol Exp Ther. Aug. 1999; 290:871–880.*

Gisele Sarosy and Eddie Reed, Journal of the National Medical Association, Jun. 1993, vol. 85, No. 6, pp. 427 to 431.

* cited by examiner

Primary Examiner—Thurman K. Page
Assistant Examiner—Rachel M. Bennett
(74) Attorney, Agent, or Firm—Kenyon & Kenyon

(57) ABSTRACT

The present invention provides for a method for treating human or animal patients with paclitaxel formulation, the method comprising an intratumoral dose of a paclitaxel formulation and an intravenous dose of paclitaxel. The intravenous dose occurs about 1 to about 7 days after the intratumoral dose. The paclitaxel formulation may typically be either a paclitaxel/HSA formulation or paclitaxel/γ-globulin formulation.

20 Claims, No Drawings

METHOD OF ADMINISTRATION OF PACLITAXEL-PLASMA PROTEIN FORMULATION

CROSS-REFERENCE TO RELATED APPLICATION

This application claims the benefit of provisional application Ser. No. 60/195,912, filed Apr. 10, 2000, which is incorporated entirely herein by reference.

FIELD OF THE INVENTION

The present invention relates to the field of delivery of anti-tumor chemotherapeutics and more particularly to delivery of the anti-tumor chemotherapeutic, paclitaxel.

BACKGROUND

Paclitaxel is a high molecular weight (854 g/mole), highly lipophilic cytotoxic chemotherapeutic used as an anti-tumor agent in the treatment of carcinomas of the ovary, breast, lung and in the treatment AIDS related Karposi's sarcoma. Paclitaxel is currently used to treat breast cancer by pre-operatively administering the drug systemically. The pre-operation treatment reduces tumor burden prior to surgery, thus potentially improving the post-surgery prognosis. Although impressive success has been achieved using this approach, the treatment requires prolonged hospitalization and is accompanied by severe side-effects. Moreover, a significant number of cases (30%) do not result in a clinically satisfactory outcome either because the tumors are not reduced or because the side effects require that paclitaxel dosing be discontinued.

Paclitaxel's cytotoxic and anti-tumor properties derive from its ability to promote apoptosis (programed cell death) by inducing the assembly of microtubules from tubulin dimers and preventing microtubules from depolymerization. The stabilized microtubules inhibit normal dynamic reorganization of the microtubule network that is essential for vital interphase and mitotic functions. In addition paclitaxel induces abnormal arrays or "bundles" of microtubules throughout the cell cycle and multiple asters of microtubules during mitosis.

Paclitaxel Formulations

Paclitaxel is substantially water insoluble and must be administered using a solubilizing carrier. The currently approved paclitaxel carrier formulation, marketed as TAXOL®, comprising pacitaxel dissolved in ethanol and CREMOPHOR®EL (polyoxyethylated castor oil).

The TAXOL® carrier CREMOPHOR®EL can cause side effects, such as anaphylaxis and severe hyper-sensitivity. (Sarosy and Reed, *J Natl Med Assoc* (1993) 85(6):427–31.) To reduce the side effects, current recommended treatment with TAXOL® includes pre-medication with corticosteroids, diphenhydramine and $H_2$ antagonists.

Several alternative carriers have been proposed to address the anaphylaxis and severe hyper-sensitivity caused by the CREMOPHOR®EL. For example, U.S. Pat. No. 5,684,169, which is incorporated by reference, discloses unbranched cyclodextrin or branched cyclodextrin inclusion complexes of paclitaxel which improves the solubility of paclitaxel in water. The complex is produced by adding an unbranched cyclodextrin or a branched cyclodextrin to paclitaxel at a molar ratio of 1–20 times with respect to paclitaxel. By improving solubility, the cyclodextrin inclusion complex improves paclitaxel absorption in cancer patients.

U.S. Pat. No. 5,415,869, which is incorporated by reference, discloses paclitaxel or paclitaxel tumor-active analogs solubilized using one or more negatively charged phospholipids and one or more zwitterionic phospholipids. The phospholipid mixture entraps paclitaxel or the analog in a liposome. The liposome is in the form of particles having a size of 0.025 to 10 microns, with substantially no crystals of paclitaxel or the analog.

U.S. Pat. No. 5,580,575, which is incorporated by reference, discloses a therapeutic drug delivery system comprising gas-filled microspheres and a therapeutic drug, as well as, methods for employing such microspheres in therapeutic drug delivery. The preferred microspheres of the disclosure are gas-filled liposomes with an encapsulated drug. Methods of preparing such liposomes in drug delivery applications are also disclosed.

WO 99/13914, incorporated herein by reference, discloses that paclitaxel, and other slightly water soluble drugs can be formulated without CREMOPHOR®EL or other toxic solubilizers by forming a water soluble homogeneous complex with plasma proteins, such as human serum albumin (HSA) or human gamma globulin (γ-globulin). As disclosed by WO 99/13914 homogeneous aqueous solutions up to at least 4.68 mM paclitaxel (4 mg/mL) can be formulated using HSA. The plasma proteins act as a slow release depot of paclitaxel. WO 99/13914 further discloses a dosage range of paclitaxel-HSA complex containing 70–280 mg of paclitaxel per treatment. Such formulations can be made bio-equivalent to the conventional CREMOPHOR®EL containing formulations.

Other formulations for administering paclitaxel are disclosed in U.S. Pat. Nos. 5,504,102 and 5,407,683, incorporated herein by reference.

In addition, the slow infusion of CREMOPHOR®EL solutions has been studied as a means of avoiding or ameliorating the side effects of the CREMOPHOR®EL vehicle. The most common dosage is 135–175 mg/m$^2$ CREMOPHOR®EL, which is administered over a 3 hour, 6 hour, or 24 hour dosage schedule. (See U.S. Pat. Nos. 5,641,803, and 5,621,001, both incorporated herein by reference.) Other dosing schedules have been suggested to reduce toxic side effects, including 96 hour infusion every 21 days (U.S. Pat. No. 5,496,846, incorporated herein by reference) and 60–180 minutes, repeated a plurality of times during a 21 day period, each infusion separated by an interval of between 4 to 5 days. (U.S. Pat. No. 5,696,153, incorporated herein by reference).

Paclitaxel Chemotherapy Reservoir

An alternative method of administering paclitaxel is using a chemotherapy reservoir. U.S. Pat. Nos. 5,846,565, 5,626,862 and 5,651,986, which are incorporated by reference, discloses a method and devices for localized delivery of a chemotherapeutic agent to solid tumors, where the chemotherapeutic agent does not cross the blood-brain barrier and is characterized by poor bioavailability and/or short half-lives in vivo. The devices consist of reservoirs which release the chemotherapeutic over an extended period while at the same time preserving the bio-activity and bio-availability of the agent. The preferred embodiment is biodegradable polymeric matrices. Alternatively reservoirs can be made from non-biodegradable polymers or reservoirs connected to implanted infusion pumps. The devices are implanted within or immediately adjacent to the tumors to be treated or the site where tumors have been surgically removed. The patents further disclose the efficacy of paclitaxel and camptothecin delivered in polymeric implants prepared by compression molding of biodegradable and non-biodegradable polymers, respectively.

U.S. Pat. No. 5,888,530, which is incorporated by reference, discloses a method of enhancing the amount of a pharmaceutical composition delivered to a target tissue site in a mammal, by creating a transient differential between the hydrostatic pressure in the target site and a region near the target tissue site. An apparatus for performing the method is provided. In one form that apparatus includes a pharmaceutical reservoir, pump, and an agent reservoir and pump.

Chemotherapy reservoirs are also disclosed in U.S. Pat. No. 5,470,311 incorporated herein by reference.

Initial results testing such chemotherapy reservoirs have been disappointing. While a significantly lowered side effect profile has been demonstrated, there are no indications of clinical improvement.

The limitations of current chemotherapy reservoir technology is probably due to the retention of the chemotherapeutic drug only on the tumor periphery or at the injection site due to the poor penetration and distribution of the drug as a result of the neoplasm's high interstitial fluid pressure. A more potent anti-tumor effect can be achieved by targeting the chemotherapy directly to the tumor, i.e., intratumorally, rather than by systemic infusion.

We now report a method of delivering an anti-cancer chemotherapeutic, such as paclitaxel, by first administered paclitaxel by intratumoral injection and thereafter administering paclitaxel by intravenous injection. This invention takes advantage of the lower toxicity and side effects of paclitaxel/plasma solutions, and the ability of plasma proteins, such as HSA, to act as a slow release depot for paclitaxel.

SUMMARY OF THE INVENTION

The present invention provides for a method of delivering paclitaxel, the method comprising an intratumoral dose of a paclitaxel formulation and an intravenous infusion of paclitaxel wherein the intravenous infusion occurs about 24 hours to about 7 days after the intratumoral dose.

DETAILED DESCRIPTION OF THE INVENTION

The present invention provides for a method of delivering a paclitaxel. According to the invention paclitaxel, as a paclitaxel formulation, is first brought into contact with substantially all the cells of a solid tumor, by an intratumoral dose. Thereafter paclitaxel is administered by intravenous infusion. The paclitaxel administered by intravenous infusion may be the same paclitaxel formulation used in the intratumoral dose. Alternatively, the paclitaxel may be administered by infusion of paclitaxel in any other soluble form.

While not being bound by theory, it is believed that the intratumoral dose of the paclitaxel formulation induces apoptosis within the tumor by slowly releasing paclitaxel into the tumor over a period of twenty-four hours to one week. The cell death that occurs within the tumor results in the collapses of the tumor structure. The collapsed tumor allows access of the second intravenous dose of paclitaxel to reach inside the partially collapsed tumor structure. One of skill in the art will recognize that, the invention is not limited to methods which function in this manner.

Intratumoral Dose of Paclitaxel Formulation

One aspect of the present invention provides for introducing a paclitaxel formulation intratumorally. For example, in one embodiment of the present invention, the intratumoral dose of paclitaxel formulation may be injected intratumorally using a syringe pump. The flow rate and pressure of the syringe pump will depend upon the tumor to be treated. The flow rate of the syringe pump may vary from about 0.0167 ml/min to about 0.5 ml/min. The preferred flow rate will deliver the paclitaxel formulation to greater than 90% of the tumor volume while delivering essentially no paclitaxel outside the tumor.

The paclitaxel formulation is preferably a soluble form of paclitaxel comprising a paclitaxel/plasma protein complex. As used herein, paclitaxel/plasma protein complex refers to paclitaxel in a water-ethanol solution containing a solubilizing amount of plasma protein wherein the paclitaxel forms a non-covalent complex with the plasma protein. Preferably the plasma protein is HSA or $\gamma$-globulin. Most preferably the plasma protein is HSA. One of skill in the art will understand that paclitaxel/plasma protein is not limited to the use of these two proteins and includes any plasma protein capable of forming a non-covalent paclitaxel/plasma protein complex and thereby solubilizing paclitaxel.

While not being bound by theory, it is proposed that administering a soluble form of paclitaxel, such as a paclitaxel/plasma protein complex, increases drug efficacy by promoting paclitaxel diffusion. Increased diffusion promotes apoptosis tumor cell death not only in the immediate zone of the injection but also at sites further into the tumor where the paclitaxel has migrated.

The mass of paclitaxel formulation delivered intratumorally depends upon the size of the tumor, and can range up to about 280 mg of paclitaxel. Preferably, the intratumoral mass of paclitaxel is from about 1 to about 60 mg of paclitaxel.

The volume of the dose is preferably about $\frac{1}{4}$ to about $\frac{1}{12}$ the tumor volume. Most preferably the volume of the dose is about $\frac{1}{10}$ of the tumor volume.

The preferred concentration of the paclitaxel formulation is about 4 to about 10 mg/ml of paclitaxel, or about 3.4 to about 8.5 mM paclitaxel.

Thus, a tumor with a 4 cm diameter has a volume of 33 cc. Consequently, a 6 ml of a 10 mg/ml dose of paclitaxel liquid delivered into the tumor results in a dose of 60 mg paclitaxel which is approximately the maximal intratumoral injection dose.

If the initial intratumoral administration of the paclitaxel formulation does not substantially shrink the solid tumor, an additional intratumoral dose of the paclitaxel formulation may be administered. The additional intratumoral dose may be at an identical, at a greater, or at a lower concentration of the paclitaxel formulation then the initial intratumoral dose. In one embodiment of the present invention, the paclitaxel/ plasma protein may be administered by multiple intratumoral injections within a short period of time. The invention provides for multiple intratumoral injections of the paclitaxel formulation administered within 24 hours.

While not being bound by theory, administering the paclitaxel formulation by frequent intratumoral injections may increase the efficacy of paclitaxel by inducing apoptosis at various stages of the cell cycle.

Intravenous Infusion of Paclitaxel

Methods of delivering an anti-tumor chemotherapeutic by intravenous infusion are well known in the art and are described for example in U.S. Pat. Nos. 5,696,153, 5,496,846, and 5,641,803.

In one embodiment of the present invention, the paclitaxel is administered by intravenous infusion about twenty-four hours to about 1 week following the intratumoral dose as a continuous infusion. The intravenous dose is typically administered over about 3 to about 12 hours. The paclitaxel administered by intravenous infusion may be the paclitaxel formulation used in the intratumoral dose administered as a saline solution of 5% dextrose or normal saline. Alternatively, the paclitaxel may be administered by infusion of paclitaxel in any other soluble form.

When the paclitaxel administered by intravenous infusion comprises the paclitaxel/plasma protein complex, the intratumoral or the intravenous treatment may be repeated in cycles. The administration of the paclitaxel/plasma protein complex may be repeated because of the decreased hypersensitivity reaction from the paclitaxel paclitaxel/plasma protein complex compared to TAXOL®.

In one embodiment, the intravenous infusion of paclitaxel comprises administering a plurality of repeated intravenous infusions subsequent to the intratumoral dose, wherein each infusion is separated by about seven days.

Another embodiment comprises administering an additional intravenous infusion of the paclitaxel formulation, about 4 to about 21 days subsequent to the intravenous infusion.

Another embodiment comprises an additional intratumoral dose administered subsequent to the intravenous dose. The additional intratumoral dose is preferably administered about 4 to about 21 days subsequent to the intravenous infusion.

In an alternative embodiment of the invention, the intravenous dose may be administered by solubilizing paclitaxel in CREMOPHOR®EL ethanol solutions. The solution of this embodiment comprises 6 mg/mL paclitaxel, corresponding to a paclitaxel concentration of about 7 mM, which is diluted prior to infusion with 0.9% sodium chloride injection, U.S.P, 5% dextrose injection, U.S.P, 5% dextrose and 0.9% sodium chloride injection, U.S.P, or 5% dextrose in Ringer's injection to a final concentration of 0.3 to 1.2 mg/mL. The maximum TAXOL® concentration which can be administered by intravenous infusion using this formulation is about 0.6 mg/mL.

The intravenous dose is preferably in the range of about 100 to about 200 mg/m$^2$. More preferably the intravenous dose is in the range of about 135 to about 175 mg/m$^2$.

The mass of paclitaxel administered by intravenous infusion is preferably between about about 70 to about 280 mg.

The function and advantage of these and other embodiments of the present invention will be more fully understood from the examples below. The following examples are intended to illustrate the benefits of the present invention, but do not exemplify the full scope of the invention.

EXAMPLES

EXAMPLE 1

Improved Spread of Evan's Blue-Albumin in a Human Mammary Adenocarcinoma MCF7 Xenograft in Immunocompromised Mice when Injecting Intratumorally Under Pressure as a Model for Paclitaxel/HSA Spread in the Tumor.

Purpose

The purpose of the study is to assess the efficiency of spread of a solution of Evan's blue dye—albumin complex in a tumor when injected intratumorally at different flow rates. The complex of the dye with albumin serves as a model of the complex of paclitaxel with albumin and allows visualization of the complex spread within the tumor.

Methods and Results

Nude (athymic mice) (~5 weeks of age) were injected subcutaneously with a cell suspension containing approximately $10^7$ cells/0.1 ml of human mammary tumor cell line MCF7. On Day 28 following tumor cell implantation, all tumors were measured as described below, and the measurement recorded for each mouse as the pre-treatment baseline tumor volume. Tumor measurement were performed using calipers, to measure the tumor in two dimensions, at approximately 90°. to each other, at the longest and widest points. The tumor volume was calculated according to the formula, $(W^2 \times L)/2$, where W is the tumor measurement at the widest point, and L is the tumor dimension at the longest point.

Mice with tumor volumes within the range of 5–8 grams were allocated to the study. The mice were injected intratumorally with 1 ml of a solution of Evan's blue albumin in buffered saline using a Sage Instrument Model #355 syringe pump. The albumin dye complex serves as a visual model for the albumin paclitaxel complex. The solution was injected into the tumor at various flow rates between 0.0167 ml/min to 0.5 ml/min which corresponded to various back pressures. The faster the flow rate the higher the (not measured) back pressure is presumed to be. The flow rates tested were:

| Flowrate |
|---|
| 0.0167 ml/min (1 ml/60 min) |
| 0.05 ml/min (1 ml/20 min) |
| 0.1 ml/min (1 ml/10 min) |
| 0.2 ml/min (1 ml/5 min) |
| 0.5 ml/min (1 ml/2 min) |

After the injections the mice were sacrificed, the tumor removed and the extent of the spread of the blue dye in the tumor measured visually.

From the results are given in the following table. One can see that the raising of the pressure results in a more efficient spread of the dye.

| Flow rate | Percent of tumor volume dyed |
|---|---|
| 0.0167 ml/min (1 ml/60 min) | 2–5 |
| 0.05 ml/min (1 ml/20 min) | 20–40 |
| 0.1 ml/min (1 mi/10 min) | 40–60 |
| 0.2 ml/min (1 mi/5 min) | 70–90 |
| 0.5 ml/min (1 mi/2 min) | >90 |

Conclusion

The results exemplify that the albumin can be effectively spread within the entire tumor volume when the pressure of the infusion is slightly raised. In our system, a flow rate of 0.2 ml/min suffices to raise the pressure and spread the soluble albumin complex. The efficient spread of the paclitaxel albumin complex results in more efficacious treatment of the solid tumors.

EXAMPLE 2

In Vivo Evaluation of the Anti-Tumor Effect of Intratumoral Injections of Paclitaxel/HSA in Human Breast Tumor (Cell line MCF7) Xenografts in Nude Mice, Purpose of Study The purpose of the study is to assess the anti-tumor effect of intratumoral injections of Paclitaxel/HSA, a novel proprietary compound of paclitaxel complexed with human serum albumin) against a human mammary tumor xenograft (cell line MCF7) in immunodeficient mice. The potential of paclitaxel/HSA to reduce tumor size is compared to the standard chemotherapeutic agent, TAXOL®.

Methods and Results

There are five study groups containing 6–10 mice per group. The mice are allocated to the following 5 groups:

| Group Number | Drug | Dosage | Method of Administration | Number of Injections (within 24 hours) |
|---|---|---|---|---|
| I | No treatment (control) | — | — | — |
| II | Saline (control) | 0.2.ml/gm[a] | Intratumoral | 2 |
| III | TAXOL ® | 0.2 ml/gm[a] | Intratumoral | 2 |
| IV | Paclitaxel/HSA | 0.2 ml/gm[a] | Intratumoral | 2 |
| V | Paclitaxel/HSA | 0.2 ml/gm[a] | Intratumoral (via high-pressure infusion) | 2 |

[a]per gram tumor weight at 1 mg paclitaxel/ml

Nude (athymic mice) (~5 weeks of age) are injected subcutaneously with a cell suspension containing approximately $10^7$ cells/0.1 ml of human mammary tumor cell line MCF7. The mice are examined routinely for the appearance of tumors. On Day 28 following tumor cell implantation, all tumors are measured as described below, and the measurement recorded for each mouse as the pre-treatment baseline tumor volume. Tumor measurement are performed using calipers, to measure the tumor in two dimensions, at approximately 90° to each other, at the longest and widest points. The tumor volume are calculated according to the formula, $(W^2 \times L)/2$, where W is the tumor measurement at the widest point, and L is the tumor dimension at the longest point.

All mice with tumor volumes within the range of 5–8 grams are allocated to study groups. Allocation to treatment groups are carried out based on the volume of the individual tumors, with each study group receiving an approximately equal representation of all tumor volumes. At study baseline, Day "0" of the Treatment Phase, all mice are receive the first injection according to their study group assignment. Approximately twenty-three hours later, the tumors are measured as described above, and the volumes recorded. Immediately following measurement, within 24 hours of the first injection, the mice are receive a second injection according to the study group assignment. Post-treatment tumor volumes are assessed at 48 hours, 7 days, 14 days, and 21 days following the initial injection. The mice are sacrificed and the tumors removed and weighed. The final weights for each treatment group are averaged and compared to the final weights obtained for the "no-treatment" group.

For each mouse within a study group, the post-treatment tumor volumes just before the $2^{nd}$ injection at 24 hours, and at 48 hours, 7, 14 and 21 days following the initial injection, are measured and recorded. The relative tumor volume (post-treatment tumor volume/pre-treatment baseline tumor volume) are recorded at each time point, and the mean relative tumor volume for each time point, for all mice within a study group, are determined. Additionally, following sacrifice, the final weights for the tumors for each study group are averaged and compared to the final weights observed for the "no-treatment" group.

The expected results of the measurement of relative tumor volume (100×post-treatment tumor volume/pre-treatment baseline tumor volume) (expected results) are tabulated in the following table:

| Group | % tumor volume at 2 days | % tumor volume at 7 days | % tumor volume at 14 days | % tumor volume at 21 days |
|---|---|---|---|---|
| I | 105 | 125 | 150 | 175 |
| II | 105 | 125 | 150 | 170 |
| III | 50 | 50 | 75 | 85 |
| IV | 40 | 40 | 60 | 75 |
| V | 40 | 25 | 25 | 40 |

Conclusion

Intratumoral injections of soluble paclitaxel/HSA are an effective method of affording tumor shrinkage. Two intratumoral injections separated by 24 hours are effective in shrinking the tumor to about 40% of its original value. Elevated pressure makes the injections more effective. Further injections, in an improved protocol, could conceivably bring about a full remission in the tumor.

What is claimed is:

1. A method of administering paclitaxel to a patient having a tumor, the method comprising;
   introducing an intratumoral dose of a paclitaxel formulation; and,
   subsequently providing an initial intravenous infusion of paclitaxel about 24 hours to about 7 days after the intratumoral dose.

2. The method of claim 1, wherein the paclitaxel formulation is a mixture of paclitaxel and plasma protein in an amount effective to solubilize the paclitaxel.

3. A method of treating a patient having a tumor comprising:
   administering to a tumor at least one intratumoral dose of a first formulation comprising paclitaxel and a plasma protein, thereby inducing apoptosis; and
   administering intravenously to a patient at least one dose of a second formulation comprising paclitaxel, the first dose of the second formulation occurring about 1 to about 7 days after the the intratumoral dose,
   wherein the first and second formulations are the same or different, and
   wherein the amount of plasma protein in the first formulation is an amount effective to solubilize the paclitaxel.

4. The method of claim 3, wherein the plasma protein is selected from the group consisting of human serum albumin and γ-globulin.

5. The method of claim 3, wherein the dose of paclitaxel formulation is between about 1 to about 60 mg of paclitaxel.

6. The method of claim 3, wherein the paclitaxel formulation is between about 4 to about 10 mg/ml paclitaxel.

7. The method of claim 3, wherein the intratumoral dose is administered by a plurality of injections of the paclitaxel formulation.

8. The method of claim 3, wherein the intratumoral dose of the paclitaxel formulation is administered by syringe pump.

9. The method of claim 3, wherein the intravenous infusion of paclitaxel comprises administering between about 70 to about 280 mg of paclitaxel.

10. The method of claim 3, wherein the intravenous infusion of paclitaxel comprises administering between about 100 to about 200 mg/m$^2$ of paclitaxel.

11. The method of claim 3, wherein the intravenous infusion of paclitaxel comprises administering between about 135 to about 175 mg/m$^2$ of paclitaxel.

12. The method of claim 3, wherein the intravenous infusion of paclitaxel comprises administering a mixture of paclitaxel and plasma protein in an amount effective to solubilize the paclitaxel.

13. The method of claim 12, wherein the solubilizing plasma protein is selected from the group consisting of human serum albumin and γ-globulin.

14. The method of claim 1, wherein the intravenous infusion of paclitaxel comprises administering paclitaxel and polyoxyethylated castor oil.

15. The method of claim 3, wherein the intravenous infusion of paclitaxel comprises administering a plurality of intravenous infusions subsequent to the intratumoral dose.

16. The method of claim 3, further comprising administering an additional intravenous infusion of the paclitaxel formulation subsequent to the intravenous infusion.

17. The method of claim 16, wherein the additional intravenous dose is administered about 4 to about 21 days subsequent to the intravenous infusion.

18. The method of claim 16, further comprising administering an intratumoral dose of the paclitaxel formulation subsequent to the additional intravenous infusion.

19. The method of claim 3, further comprising administering an additional intratumoral dose of the paclitaxel formulation subsequent to the intravenous infusion.

20. The method of claim 19, wherein the additional intratumoral dose is administered about 4 to about 21 days subsequent to the intravenous infusion.

* * * * *